United States Patent [19]

Simpson et al.

[11] 4,148,859
[45] Apr. 10, 1979

[54] BACKWASH SYSTEM FOR DILUTING APPARATUS

[75] Inventors: Ronald O. Simpson; Pedro P. Cabrera, both of Miami, Fla.

[73] Assignee: Coulter Electronics, Inc., Hialeah, Fla.

[21] Appl. No.: 906,235

[22] Filed: May 15, 1978

[51] Int. Cl.² ............................................. G01N 1/14
[52] U.S. Cl. ................................ 422/103; 73/422 R; 422/100
[58] Field of Search ............................ 23/253 R, 259; 73/422 R

[56] References Cited

U.S. PATENT DOCUMENTS

| | | | |
|---|---|---|---|
| 3,567,389 | 3/1971 | Coulter et al. | 23/259 Y |
| 3,567,390 | 3/1971 | Rothermel | 23/259 |
| 3,652,228 | 3/1972 | Bernard | 23/253 R |
| 3,976,429 | 8/1976 | Ginsberg | 23/259 |
| 3,990,853 | 11/1976 | Godin | 73/422 R X |
| 3,991,055 | 11/1976 | Godin et al. | 23/259 |

*Primary Examiner*—R. E. Serwin
*Attorney, Agent, or Firm*—Silverman, Cass & Singer, Ltd.

[57] ABSTRACT

Improvements in a backwash system for diluting apparatus wherein a rinse solution is directed to the fluid transfer valve thereof and thence back to and through the sample pick-up probe to a receptacle and then to a waste depositary. The receptacle is mounted on a carrier, in turn mounted for movement in a track from a recessed condition, along a path directed first outward and then upward to engage the delivery end of the sample probe in a fluid tight sealed coupling. A plunger of an air cylinder effects the movement of the receptacle in the track. A vacuum operated switch is employed to assure that the rinse solution will not be dispensed as backwash unless the sealed coupling is made. Alternatively, a microswitch can be substituted for the vacuum operated switch and presented in the path of the carrier to be actuated when the carrier has moved sufficiently to establish the sealed coupling between the receptacle and the delivery end of the sample probe. In either instance, the switch is scanned to ascertain its state and unless actuated, backwash is prevented.

19 Claims, 5 Drawing Figures

BACKWASH SYSTEM FOR DILUTING APPARATUS

CROSS-REFERENCE TO RELATED PATENTS

This patent application presents improvements in a backwash system of the type disclosed in U.S. Pat. No. 3,976,429 dated Aug. 24, 1976, the same being hereby incorporated by reference in this application to supply additional background and explanation herein.

U.S. Pat. Nos. 3,549,994 and 3,567,390 dated respectively Dec. 22, 1970 and Mar. 2, 1971 likewise are incorporated by reference herein to serve as explanation of the types of apparatus in conjunction with which the improved backwash system can be employed.

BACKGROUND OF THE INVENTION

This invention relates generally to apparatus which utilizes vessels, valves and connecting conduits for the intermixing and/or diluting of fluids primarily for the purpose of making measurements and tests upon said fluid. More particularly, this invention is concerned with the type of automatic analysis instrument such as disclosed in U.S. Pat. Nos. 3,549,994 and 3,567,390 which employ the Coulter particle analyzing principle disclosed in U.S. Pat. No. 2,656,508. In particular, the invention herein provides improvements to the backwash system for diluting apparatus disclosed in U.S. Pat. No. 3,976,429 issued Aug. 24, 1976, owned by the assignee of this application.

In U.S. Pat. No. 3,976,429, a backwash system was provided, including a dispensing cylinder and valve arrangement for directing diluent as a backwash from a source to a sampling valve utilized to make dilutions and then to a sampler in a form of an aspirator tube introduced into a fluid, and a vessel was provided for catching the backwash fluid. Means were provided for aspirating the backwash fluid to waste. The vessel and the aspirator tube were positioned one relative to the other to enable the backwash to be received in the vessel only when diluent was dispensed as backwash. One of the aspirator tube and collector vessel was returned to its so-called normal condition relative the other either by movement of the tube relative to the collector vessel, or by movement of the collector vessel relative to the tube. Suitable controls were provided to assure that the backwash occurs only when the tube and vessel were in a relative relationship to receive the backwash.

One structure described in the last-mentioned patent comprises a receptor vessel in the form of hollow, segmentally configured vessel having an inlet opening in one wall thereof. The vessel was mounted pivotally for selective limited rotation about an axis taken through a corner thereof. Gears were provided to effect pivotal movement of the vessel about the mounting axis to align the inlet opening with the aspirator tube so that backwashed diluent could be delivered from the aspirator tube to the inlet opening. The backwashed diluent received in the collector vessel was removed therefrom by drawing a vacuum upon the vessel, the line leading to a waste container distant from the apparatus.

Some problems have been encountered during use of said backwash system. One problem involves the manipulation of the receptacle from an inactive to a backwash receiving condition. The inlet opening of the receptacle had to be placed into a disposition proximate to the delivery end of the aspirator tube but was spaced therefrom. Thus in the course of delivery, some splashing would occur. Not only was there a chance that some delivered fluid would be lost but the problem of contamination of the environment is present This is of particular disadvantage where the contents include contagions such as, for example, hepatitis causing organisms, possibly corrosive or chamically active fluids.

In the last mentioned patent, vacuum was only utilized to draw the backwash from the receptacle or collector vessel to a waste container. It also is important to provide means, as a part of the backwash system, to assure that the backwash be effected only when a sealed connection has been effected between the delivery end of the aspirator tube and the means provided to receive the backwash fluid and the residual material driven out thereby.

SUMMARY OF THE INVENTION

A backwash system for a diluting apparatus of the type including a source of rinse fluid, a sample probe, a liquid transfer valve, a first flow path between said sample probe and said liquid transfer valve, means operable to draw a liquid sample along said first flow path to said sample transfer valve, said transfer valve being operable between a first sample receiving condition and a second condition whereupon a volume of the sample drawn from the first flow path is discharged along with a given volume of diluent along a second flow path to a testing apparatus. The valve is returned to its sample receiving condition and backwash is effected by introducing rinse fluid from a source thereof to the valve from which the rinse fluid is directed back along the first flow path to and through the sample probe, and from the delivery end thereof, to a waiting receptacle from whence it is delivered to waste. The receptacle is mounted on a carrier and moved along a predetermined path first outward, then upward to engage the delivery end of the sample probe. The path of movement of the carrier properly to place the receptacle is defined by guide means, including a track formed in a pair of guide plates. The receptacle includes a resilient insert at its mouth capable of effecting a fluid tight sealed connection between the delivery end of the probe and the receptacle while reducing the mechanical shock of effecting such engagement. A vacuum operated switch or a microswitch is provided to guard against premature delivery of rinse fluid in the backwash cycle, that is to permit delivery only if and when the receptacle is in proper position, sealingly coupled to the delivery end of the sample probe, the respective switch functioning in a fail safe sensing capacity.

DESCRIPTION OF PREFERRED EMBODIMENTS

At the outset it would be convenient to outline the general scheme of the system of the invention by explaining the functions which are performed.

A fluid sample is obtained in any convenient manner.

An aspirator tube, sometimes referred to hereinafter as a sample probe, is introduced into the sample and a quantity of the sample is drawn into a first portion of the fluid transfer valve of the system. The valve operates to segment a minute measured part of the sample therein and such part is diluted with a predetermined quantity of diluent. The resulting suspension is transferred with the added diluent then to a testing apparatus wherein one or more tests or operations can be performed thereon. In the system of U.S. Pat. Nos. 3,549,994 and 3,567,390 a portion of a first diluted solution is taken from the first testing apparatus to the valve and directed, with a precise volume of diluent, into a second testing apparatus. Subsequent to segmentation and transfer, the valve is returned to its initiate or "sampling" position.

The backwash system according to the invention can be employed in another diluting system wherein a pair of different dilutions can be formed from the sample of whole blood by measuring and combining with diluent different volumes of said sample. These dilutions can be effected at the same time, with the sample and diluent units being directed simultaneously respectively to the pair of testing locations. The transfer valve returns to its initiate position and backwash therethrough can be effected.

With the last mentioned diluting system, only one backwash pump need be used for delivering rinse liquid to the two measuring portions of the valve simultaneously.

A detailed description and explanation of the structure and operation of diluting systems of the type described as well as the combination therewith, of testing apparatus operating on the Coulter principle is set forth in said U.S. Pat. Nos. 3,549,994; 3,567,390 and others. Principally, reference is made to U.S. Pat. Nos. 3,549,994 and 3,567,390 and each is hereby incorporated by reference herein as a part hereof.

In the system described in these patents, the sample consisted of whole blood. The blood sample tended to remain in the aspirator tube, and in the sample receiving portion of the transfer valve. Removal thereof from the aspirator tube was dependent upon the great volume of the next sample acting as a flushing agent. Additionally, the fluid transfer valve also required flushing to free same from the residual portions of the older sample whereby to prevent partial mixing or carry-over of successive samples. Obviously, carry-over of a part of a preceding sample will result in chance of error, particularly if there is much difference in characteristics between samples.

In U.S. Pat. No. 3,976,429 there was provided means for backwashing diluent in premeasured quantities through the fluid transfer valve and the aspirator tube in a predetermined time relationship relative to the programmed operations, and, likewise, means were provided to coordinate the collection of the backwash and disposition of same, with the backwashing operation.

In the system provided in referenced U.S. Pat. No. 3,976,429, diluent was backflowed through the sample receiving passage of the fluid transfer valve to the sample probe which was utilized for sample intake. Coordinated with such operation, a waste collector vessel was arranged for disposition for receiving the backwash from the delivery end of the sample probe. The pivotally mounted collector vessel was mounted on a spring biased shaft, and caused to pivot at the time when the backwash is effected. The collector vessel is coupled to a source of vacuum for directing the collected fluid to waste and a pump was used to drive the diluent to the receptacle.

Figure 1:
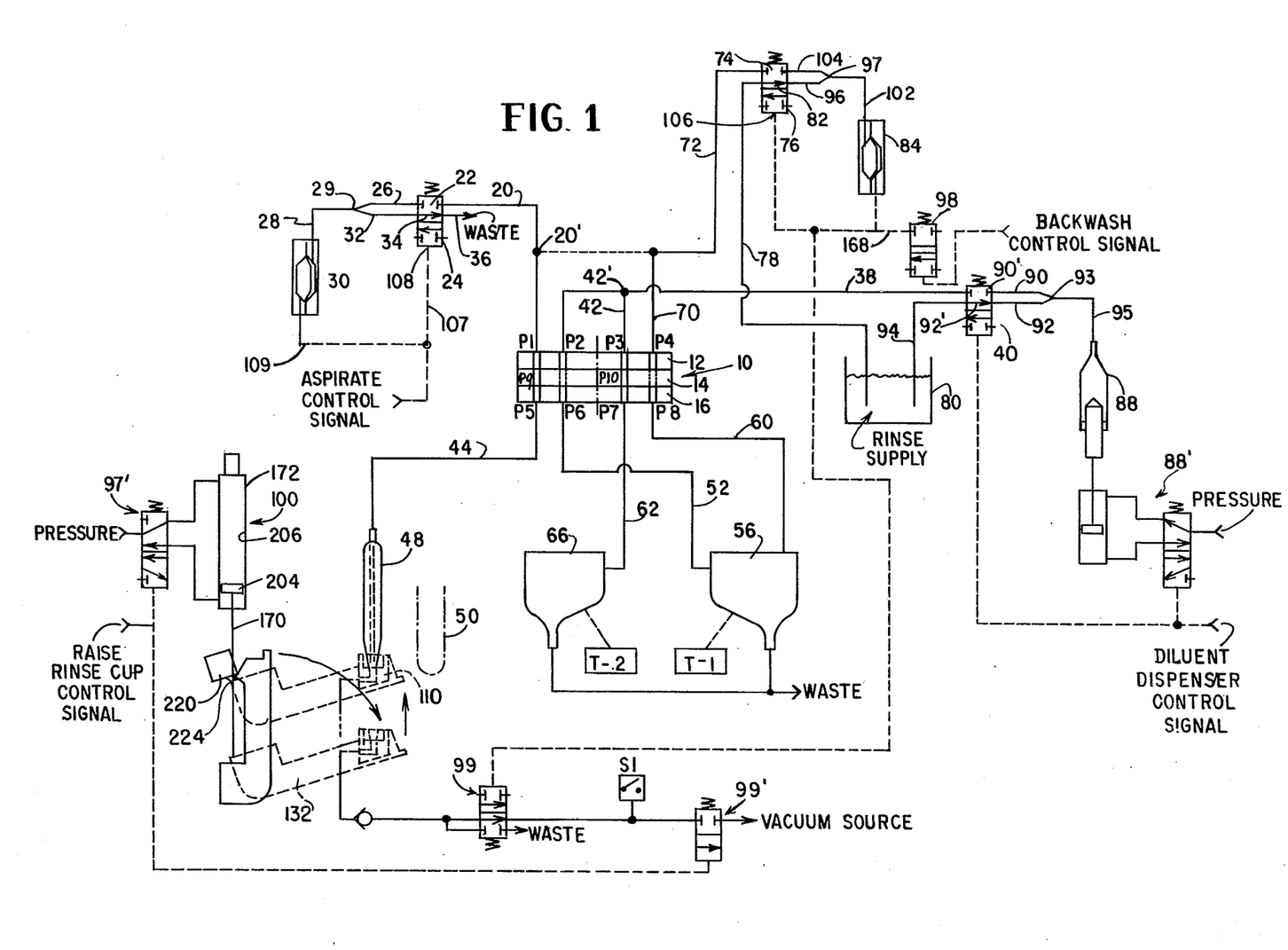
FIG. 1 is a diagrammatic representation of one diluting system having the improved backwash system of the invention associated therewith.

Referring to FIG. 1, there is illustrated diagrammatically a diluting system similar to the system illustrated and described in U.S. Pat. Nos. 3,567,390 and 3,976,429. The control or fluid transfer valve provided for the careful measurement of the sample is designated generally by the reference character 10. Valve 10 is formed of three elements, an intermediate or center element 14 movable with respect to stationary outer elements 12 and 16. The elements 12, 14 and 16 are arranged coaxially. The sandwiched or central element 14 is a carefully made and highly accurate structure having conduits P-9 and P-10, each on opposite sides of a central axis about which it is adapted to rotate. Each of these conduits is designed to carry a precise quantity or volume of some fluid, and upon movement between positions, there being two such positions, will slice off or subtend within itself the said volume of fluid and pass it or transfer it. This function is represented by the dashed lines showing the alignment of the conduits P9 and P10 with others carried by the stationary sandwiching members 12 and 16 of the valve 10. Although represented in the figure as a block or rectangular configuration, the valve 10 consisting of the elements 12, 14 and 16 preferably is cylindrical in configuration in accordance with and embodying the features of the valve illustrated specifically in FIGS. 6–10 of U.S. Pat. No. 3,567,390. The fluid transfer operation of valve 10 herein shall be described by reference only to the fluid passage means defined in the valve by which the transfer is effected and the respective dilutions made, schematically shown in rectangular configuration.

The outer members 12 and 16 are fixed relative to one another and each is provided with two pairs of ports or passageways. These are designated P1, P2, P3 and P4 in element 12 and P5, P6, P7, and P8 in element 16. When the center element 14 is in one position, say the first position, the left-hand conduit or passageway P9 is aligned with the passageways P1 and P5 at the same time that the right-hand conduit or passageway P10 is aligned with the passageways P3 and P7. Rotation of the center element 14 brings the passageways P9 and P10 to the positions represented by the dashed lines. Further flow between the passageways P1 and P5 is blocked as is further flow between the passageways P3 and P7. The passageway P9 is aligned with passageways P2 and P6 and the passageway P10 is aligned with passageways P4 and P8.

Rotation of the center element 14 is effective to slice or subtend a precise volume of fluid out of one path and enable it to be inserted into the other path while blocking off the first path. This is done in both positions of the transfer valve 10.

In one system illustrated herein as an example of a diluting system in which the backwash system of the invention can be usefully employed, the various fluid lines are described hereinafter for convenience, since the described system is only an example of the environment and does not form a part of the invention herein.

Fluid line 20 connects from the passageway P1 to the normally closed conduit 22 of pneumatically operated pinch valve 24, functionally equivalent in the illustrated system to the sample control valve to which reference is made in U.S. Pat. No. 3,567,390. Conduit 26 leads by way of line 28 of Y 29 to the sample pump which is shown in the form of a diaphragm type pump 30 or which can be an aspirator cylinder. Where a diaphragm type or other positive displacement pump is used, there is a lead to a source of alternating vacuum and pressure for operating the pump. Line 32 of Y connection 29 leads to normally open conduit 34 of pinch valve 24. Conduit 34 is coupled to waste W by line 36.

The diaphram pump 30 and actuator 108 of valve 24 are coupled by lines 109 and 107 to the aspirator logic part of the overall program of the system.

Fluid line 38 connects from the passageway P2 to the line 90' of the diluent pinch valve 40.

Fluid line 42 connects from the passageway P3 to the fluid line 38 at point 42'.

Fluid line 44 connects from the passageway P5 to the sample probe or aspirator tube 48. Note that the delivery end 48' of probe 48 is adapted to dip into a sample source vessel 50 (broken outline). The vessel 50 is of any suitable construction and is withdrawn or otherwise removed when the requisite quantity of the sample has been aspirated therefrom.

Fluid line 52 connects from the passageway P6 to mixing vessel 56 for the testing apparatus T-1.

Fluid line 60 connects from mixing vessel 56 to the passageway P8 and is sometimes called a thief.

Fluid line 62 connects from the passageway P7 to mixing vessel 66 for the testing apparatus T-2.

Fluid line 70 connects from the passageway P4 also to line 20 and to the normally closed conduit 22 of sample control pinch valve 24.

Fluid line 72 leads from the normally closed conduit line 74 of control valve 76 to connect with line 20 at point 20' for diluent delivery.

Fluid line 78 leads from the diluent supply 80 to the normally open conduit 82 of the pneumatically operated pinch valve 76 functionally equivalent in the illustrated system to the sample control valve to which reference is made in U.S. Pat. No. 3,567,390. Conduit 96 leads by way of line 102 of Y 97 to the backwash dispenser which is shown in the form of a diaphram type pump 84 or, which may be a dispensing cylinder. If a diaphram pump or other positive displacement pump is used, there is a lead to a source of alternating vacuum and pressure for operating the pump. Line 104 of Y connection 97 leads to a normally closed conduit 74 of control valve 76.

The valve 24 has an intermediate condition where both conduits 22 and 34 are closed before the normally closed conduit 22 is opened. This operational characteristic assures clean separation during the operation of the valve 24.

Diluent pump 88 is connected by the lines 90 and 92 to the pinch valve 40. Pinch valve 40 may be identical in construction to pinch valves 24 and control valve 76. As mentioned, fluid line 38 is coupled to the normally closed conduit 90' of pinch valve 40. A fluid line 94 is coupled from the normally open conduit 92' from diluent supply 80. Fluid lines 90 and 92 of Y connection 93 couple valve 40 to diluent pump 88 by way of line 95. Pump 88 is operated by pressure arrangement 88'.

The sample and diluent pumps may be of any construction, but preferably are chambers having positive displacement means therein moving from end to end to displace a volume of fluid. Each pump draws into itself the same volume of fluid it is capable of pushing out.

Pump 88 may comprise a flexible diaphragm pump pneumatically operated by a source (of alternating vacuum and pressure). It has been found that a displacement pump comprising a chamber having a solid rod reciprocably driven through a seal with said chamber by an air cylinder, said cylinder being driven by introduction of pressurized air alternatively directed to either end of the cylinder is satisfactory.

The pump can include a spring to effect the return stroke which results in introduction of fluid into the last vacated chamber.

The improved backwash system of this invention is designated generally by reference character 100. The system 100 is capable of use with all the diluting systems referred to above and here is coupled operationally to the diluent supply 80. As explained above, line 78 leads from the diluent supply 80 to normally open conduit 82 of backwash fluid control valve 76. Conduit 82 is coupled to one arm 96 of Y 97, with the leg 102 connected to dispenser 84. The other arm 104 of Y 97 is coupled to normally closed conduit 74 of control valve 76 and connects by line 72 to passageway P-1 of transfer valve 10.

The cylinder 172 is controlled by the operation of a solenoid operated valve 97' to effect raising of the piston 204 and plunger 170. The carrier 132 is pivoted to cause the receptacle 110 to be moved first outward. The carrier then is raised to cause the receptacle to be brought to a sealing coupling with the delivery end of the aspirator tube 48.

At the same time, valve 99' enables a vacuum to be drawn on the passage 120 of receptacle 110. Check switch $S_1$ controls a solenoid valve 98 which controls the operation of pump 84 and, as well, operates to control operation of valve 99 to enable flow to waste. After a suitable elapse of time, the switch $S_1$ is scanned electronically, to sense if it is open or closed. If open, it indicates failure of the sealed connection between tube 48 and cup 110 to be established as a high vacuum is drawn to operate and close switch $S_1$ when a sealed engagement of receptacle and probe (tube) is established.

When proper seating is established, solenoid operated valve 98 is energized, causing the pump 84 to operate to cause rinse liquid to be dispensed; also, valve 99 is opened to enable flow to waste.

Deenergizing solenoid operated valve 97' causes the receptacle to be retracted by reverse operation of piston 204.

It should be understood, that where microswitch 220 is utilized, the effect of operation of switch $S_1$ is met by the operation of switch 220, switch $S_1$ not being used though it may be present in the system. Both switches 220 and $S_1$ can be operative as a fail safe device so that both have to operate to effect backwash.

Figure 2:
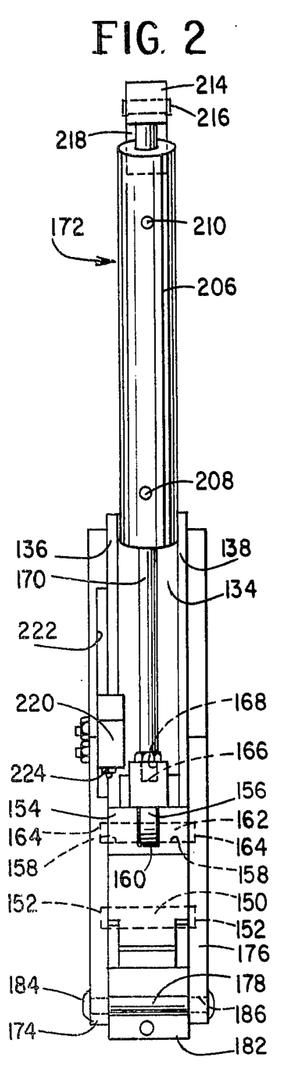
FIG. 2 is an elevational view of the collecting apparatus employed in the backwash system according to the invention.
Figure 3:
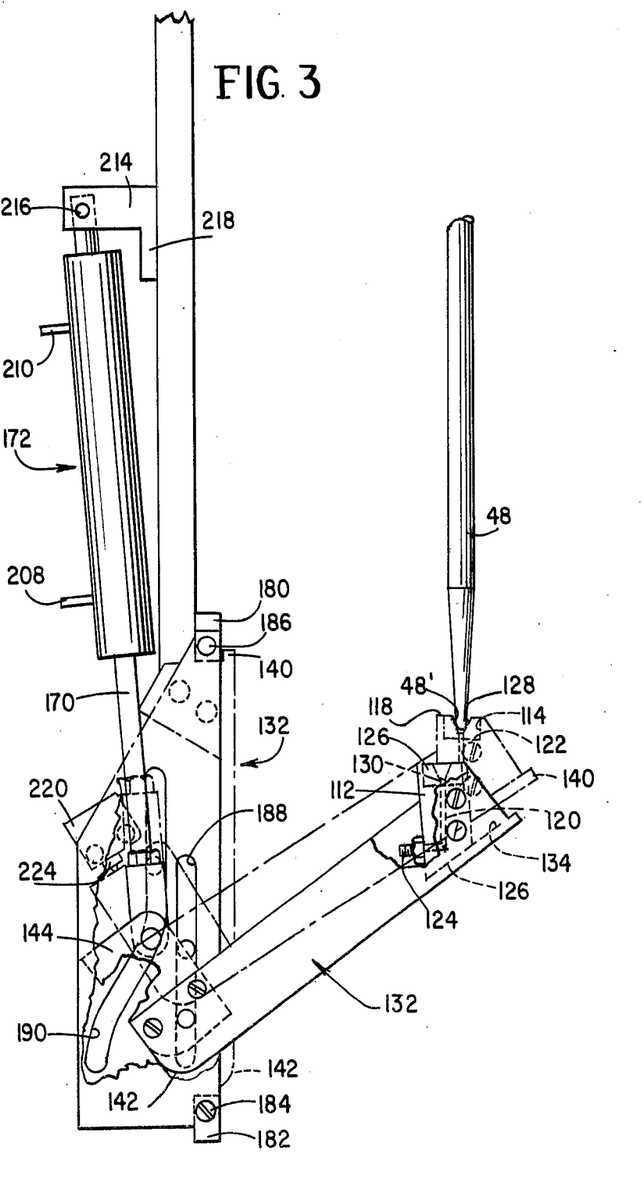
FIG. 3 is a side elevational view of the backwash collecting apparatus of FIG. 2 diagrammatically illustrating the operation thereof.

At this time attention is directed to the collector vessel 110 and its mounting as illustrated in FIGS. 2 and 3. The collector vessel 110 has a body 112 of generally rectangular configuration. A recess 114 of generally right-cylindrical configuration is formed in body 112 opening to the top wall 118 thereof. A bore 120 is formed through the body 112 communicating between the floor 122 of recess 114 and a fitting 124.

A generally cylindrical insert 126 of size and conforming configuration to recess 114 is tightly engaged within the recess 114. The insert preferably is formed of a chemically resistant material such as one of the silicone rubbers. Insert 126 has a conical recess 128 and a through passage 130 at the bottom of recess 128. When the insert 126 is seated within recess 114, the passage 130 is coaxial with and sealingly communicates with the entry to bore 120 of vessel 110, and the recess 128 opens to the top wall of vessel 110 with the insert flush with said top wall. The base 126 of vessel 110 is angular to facilitate seating of the vessel in carrier trough 132.

The carrier trough 132 is defined by planar floor 134 and a pair of upright parallel side walls 136 and 138. The floor 134 extends outward of the walls 136 and 138 to define ledge 140. The opposite end of trough 132 is rounded, as shown at 142, with the floor 134 spaced inward of the near ends of side walls 136 and 138.

Clevis block 144 is fixedly secured to the trough 132 between walls 136 and 138 thereof adjacent rounded portion 142. Coaxial passages 146 are formed in walls 136 and 138, with bore 148 (FIG. 4) formed through clevis block 144. A pin 150 is tightly seated through the said coaxial passages and bore 148, opposite ends 152 of pin 150 extending outward from the walls 136,138 when the clevis block 144 is installed.

Figure 4:
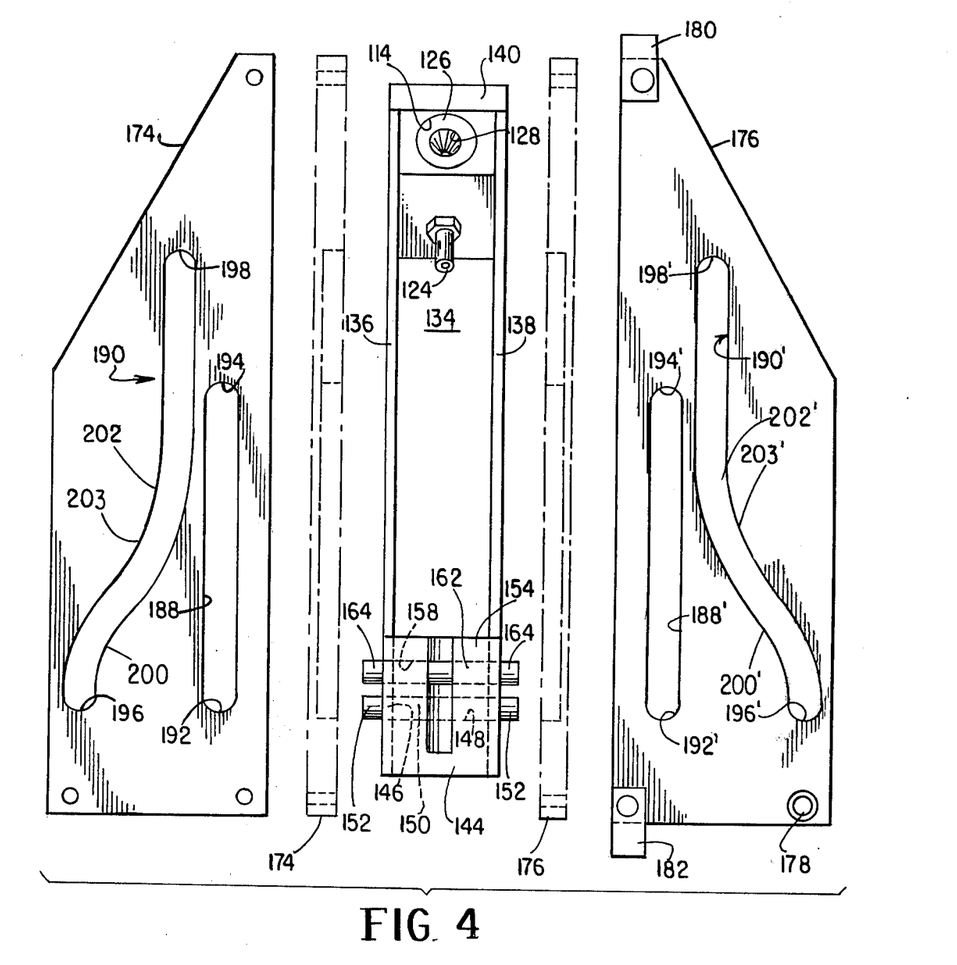
FIG. 4 is a diagrammatic partially exploded representation of the carrier, collector vessel and guide means used in the apparatus of FIGS. 2 and 3.

Clevis block 144 includes spaced wall portions 154 capable of accommodating clevis 156 therebetween. A pair of aligned passages 158 are formed through walls 154. Clevis 156 carries passage 160 which is aligned axially with passages 158. Pin 162 is seated through passages 158 and 160 to retain the clevis 156, opposite ends 164 of pin 162 extending outward on opposite sides of the clevis block. Portion 166 of clevis 156 carries a threaded socket 168 for receiving the threaded end of plunger 170 of air cylinder 172.

Referring to FIGS. 3 and 4, guide plates 174 and 176 are arranged upright and spaced apart by spacers 178, 180 and 182 and are secured fixed in such array by fastening means such as screws 184 seated in threaded passageways 186 formed in the spacers 178, 180 and 182 to define a frame. Each of the plates 174 and 176 carry a pair of grooves, 188 and 190 in plate 174, and 188' and 190' in plate 176. Grooves 188 and 188' are linear and have opposite ends 192, 194 and 192',194' respectively. Grooves 190 and 190' are longer than grooves 188 and 188'. The grooves 190 and 190' have opposite ends 196,198 and 196',198' respectively. Ends 196 and 196' are aligned and are spaced by a distance equal to the axial distance between pins 150 and 162. The distances between ends 194 and 198 and between ends 194' and 198' likewise are equal to the axial distance between pins 150 and 162. Each of grooves 190,190' have a curved portion 200 and 200' leading from ends 196,196' to a location 202,202' from whence the grooves 190,190' proceed along a line parallel to the grooves 188 and 188' to ends 194,194'.

When the plates 174 and 176 are assembled to define a frame, groove 188 and groove 190 run coextensive with groove 188' and groove 190', with the ends 152 (of pin 150) and 164 (of pin 162) seated therein, thereby defining a track along which the said pin ends can run. Ends 152 of pin 150 are seated in the grooves 188,188' while the ends 164 of pin 162 are seated in grooves 190,190'.

As illustrated in FIGS. 2 and 3, plunger 170 is secured to a piston 204 ridable within cylinder 206 which carries inlet and outlet fittings 208,210 coupled to a source of air pressure (not shown) through suitable valving and controls related to the operations of the diluent dispenser. The upper or free end is seated in clevis 214 by pin 216, clevis 214 formed on mounting member 218.

The collector vessel 110 is secured within the carrier trough 132 at the end thereof adjacent ledge 140 with the angular base 126 engaged on floor 134 so that the axis of the recess is angular relative to the walls 136 and 128 of the trough 132.

During the time of the program of the apparatus while the backwash cycle is inoperative, the trough 132 is recessed within the frame defined by the guide plates 174 and 176, the plunger 170 of air cylinder 172 being extended and the pin ends 152 seated at ends 192,192' of grooves 188,188' and pin ends 164 seated near ends 196, 196' of grooves 190,190'. Grooves 190,190' may be slightly longer than necessary to provide some over travel capability for tolerance reasons. The inward travel of trough 132 is halted when the ledge 140 strikes the surface to which spacers 180,182 are mounted. When the backwash cycle is reached, air pressure is introduced to the cylinder 106 of air cylinder 172 through inlet 208 forcing the piston 204 upward and carrying the plunger 170 into the cylinder 206. Since the clevis 156 is secured to the clevis block 144 by pin 162, withdrawal of the plunger 170 pulls the pin ends 164 along the curved portions 200,200' of grooves 190,190', with pin ends 152 remaining at ends 192,192' of grooves 188,188' and the trough 132 pivoting about said pin 150 at said groove ends 192,192'. The pin ends 164 will ride in curved portions 200,200' until a location 203,203' (near location 202,202') is reached. Continued withdrawal of the plunger 170 into cylinder 206 pulls pin ends 164 along the remaining portions of grooves 190,190'. At location 202,202', the pivotal movement of the trough 132 slows. As the ends 164 travel up the remaining portion of the curves, pivotal motion gradually decreases as pin ends 152 gradually accelerate along grooves 188,188'. The trough 132 is fully, outwardly angularly extended relatve to the guide plates 174, 176. The vessel 110 is arranged below the delivery end of the sample probe 48 with the passage 130 coaxial with the delivery end 48' of said sample probe 48.

Further continued withdrawal of the plunger 70 causes both pin ends 152 and 164 to move in unison until they approach ends 194, 198 and 194', 198' of grooves 188,188' and 190,190'. Travel is halted by the action of the probe in the rinse cup and/or the engagement of clevis 144 with the microswitch 220. Thus the delivery end of sample probe 48 engages sealingly within the conical recess 128 of insert 126 and a sealed connection is established to the bore 120 of said vessel. The continuing push of the piston 204 upwards continues the firm seating of the delivery end 48' against insert 126.

The diluent is discharged to the transfer valve 10 and backwashed through line 44 to sample probe 48 and its delivery end 48' to the bore 120 and thence to a waste depositary W. No splash occurs, of course, between the delivery end of probe 48 and the collector vessel 110. Only when backwashing is completed is air introduced into cylinder 206 by way of outlet 210 forcing the piston 204 to move in an opposite direction and causing the plunger 170 to be forced outward of cylinder 206. The pin ends are directed along the respective grooves retracing the same path in return so that the collector vessel 110 is lowered first and then the trough 132 is pivoted toward the guide plates 174, 176 to a retracted condition within the frame defined thereby.

The spacers 180 and 182 serve as mounting block means for the assembly of plates 176, 176 so that the guide plate assembly is installed upon the diluting apparatus at a location whereat the fully completed path of the carrier 132 places the collector vessel 110 in correct position to establish the sealed coupling with the delivery end of the aspirator tube 48 for the backwash cycle to be implemented.

As mentioned earlier, the microswitch 220 may be installed instead of vacuum switch $S_1$.

The microswitch 220 can be seated within a suitable recess 222 in the plate 174 with its actuator 224 seated in the path taken by clevis block 144. The actuator 224 is intercepted by block 144 when the carrier 132 of collector vessel 110 has reached its position of extension and has moved to place the pin ends 152 and 164 near the uppermost ends of their respective tracks. At this time the collector vessel 110 is capable of receiving the delivery end 48' of the aspirator tube in a sealed engagement in the conical recess 128 of insert 126.

Figure 5:
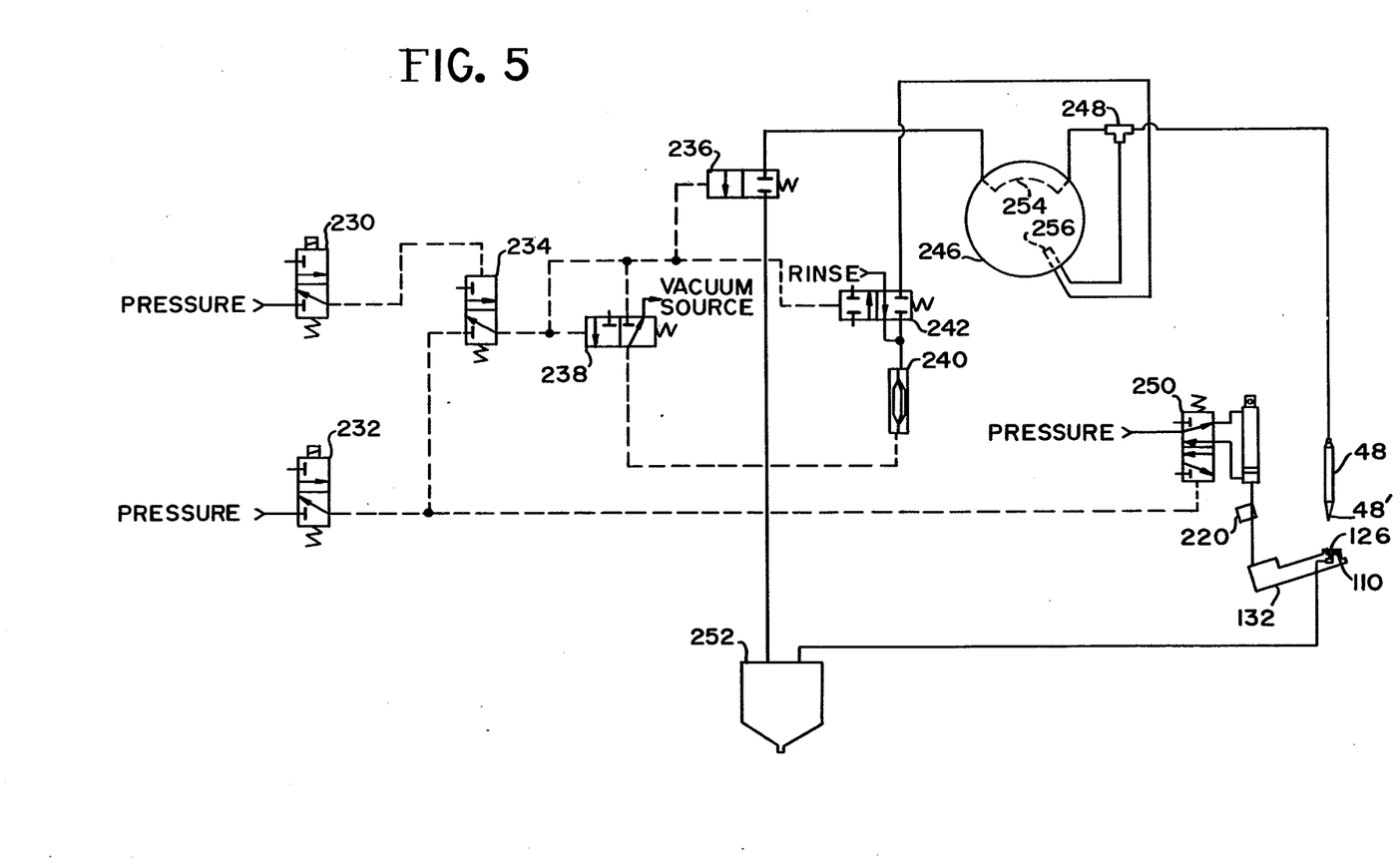
FIG. 5 is a diagrammatic representation of a modified diluting system having the improved backwash system of the invention associated therewith.

The modified diluting system with which the improved backwash system of this invention can be employed has been diagrammatically illustrated in FIG. 5 and does not employ a thief for directing a portion of the first dilution to a segmenting portion of the transfer valve for making a second dilution thereof. The required pair of different dilutions are effected simultaneously by utilizing a transfer valve 246 having passage means therein for isolating two different volumes of sample at the same time. Thus only a single pump is required to introduce rinse liquid as backwash to one portion 256 of said passage means and from there, the rinse liquid is directed through the other portion 254 of the valve 246 and thence, to the aspirator tube.

In order to avoid harmful effects possible due to surges of liquid, say due to temporary blockage in the conduit means, for example, diverter means 248 are inserted in the outlet path of the rinse liquid from valve portion 256. The flow of rinse liquid is split into two flows, one being led directly to the other measuring portion 254 of the valve while the other is directed to the backwash receptacle 110 via the aspirator tube 48. The rinse liquid outlet of said one portion 254 leads to valve 236 and thence to a waste collector 252.

In the system of FIG. 5, the solenoid 232 is operated to switch valve 250 and effectively cause the carrier 132 first to be raised placing receptacle 110 outward, and then the carrier further is moved upward to seat insert 126 against end 48' of tube 48. When the sealed connection between insert 126 and end 48' is made, switch 222 is closed. Closure of switch 222 operates solenoid 230 to open normally closed valve 234. Valve 234 is coupled to the output of valve 232. Valve 234 also operates to open both valves 236 and 242 simultaneously. These valves 236 and 242 must be open so that when the pump 240 is operated by operation of valve 238, the rinse liquid can pass to the transfer valve 246.

Actuation of valve 234 causes valve 238 to operate to dispense rinse liquid by actuating pump 240. The flow emerges from one portion of the valve 246 and is split by valve 248, one portion being directed to tube 48 and the other being directed to the other measuring portion of the valve 246 and thence back to valve 236 and waste 252. The solenoid control valve 232 then operates to lower the receptacle 110 and loads the pump 240 with a volume of rinse fluid.

The system then is ready for the next test.

What we claim is:

1. In a backwash system capable of being operationally coupled for use with a diluting system of the type providing a plurality of dilutions of differing concentration from a single liquid sample and which diluting system includes a source of fluid pressure and vacuum, a source of liquid sample and a source of diluent, a liquid transfer valve coupled to the sources of liquid sample and diluent, said transfer valve including interior precise measuring portions, for measuring and combining precise volumes of liquid sample and diluent to produce said dilutions, an aspirator including an aspirator tube having a delivery end introducible into the liquid sample and coupled to said liquid transfer valve, said backwash system arranged to pass diluent from the source thereof to the interior passageways of said liquid transfer valve, through the aspirator tube at a predetermined stage in the operation of the system, means capable of storing and delivering a known volume of diluent, a control valve including an actuator therefor positioned intermediate said diluent source and liquid transfer valve, said control valve operable between a first position only permitting passage of diluent from the diluent source to the storing and delivering means and a second position only permitting passage of diluent from the storing and delivering means to the liquid transfer valve and a collector vessel arranged to receive the backwashed liquid from the aspirator tube; the improvement comprising means mounting the collector vessel for movement along a predetermined path between a location displaced from the delivery end of the aspirator tube and a location engaging the delivery end of the aspirator tube in a sealed coupling therewith, said means including carrier means mounting said vessel, guide means defining said path, drive means coupled to a source of fluid pressure and to said carrier means for reciprocably moving said carrier means along said path and fail-safe switch means operable only upon establishment of said sealed coupling to permit delivery of diluent to the transfer valve as backwash.

2. The combination as claimed in claim 1 in which said switch means includes a check switch coupled to said actuator for enabling of same, and means coupling said vessel to said vacuum source, said means also coupled to said check switch.

3. The combination as claimed in claim 1 in which said switch means includes a microswitch coupled to said control valve, said microswitch having an actuator disposed in the path of said carrier means and engageable therewith only when said carrier means has reached a position to enable establishment of a sealed connection between the collector vessel and the delivery end of the aspirator tube.

4. The combination as claimed in claim 2 in which said means for storing and delivering diluent includes a pneumatically controlled pump, a solenoid valve to control said pump and said check switch is arranged to permit said solenoid operated pump to be energized only when the sealed connection is established and confirmed by operation of said check-switch.

5. The combination as claimed in claim 3 in which said means for storing and delivering diluent is a pneumatically controlled pump, said microswitch being arranged to permit said pump to be energized only when the sealed connection is effected between the delivery end of the aspirator tube and the collector vessel.

6. The combination as claimed in claim 1 in which said collector vessel comprises a body having a top opening recess, an internal bore leading from said recess and a resilient insert tightly seated within said recess, said insert having a top opening cavity and passage means communicating to said bore, the cavity capable of being engaged by the delivery end of the aspirator tube when said carrier reaches the terminus of its path of movement thereto to establish said sealed coupling, and means for coupling said source of vacuum to the other end of said internal bore.

7. The combination as claimed in claim 6 in which said switch means includes a vacuum operated switch coupled to said actuator for enabling of same, and means coupling said vessel to said vacuum source, said means also coupled to said vacuum actuated switch.

8. The combination as claimed in claim 7 in which said switch means includes a microswitch coupled to said control valve and having an actuator disposed in the path of said carrier means and engageable therewith only when said carrier means has reached a position to enable establishment of a sealed coupling between the collector vessel and the delivery end of the aspirator tube.

9. The combination as claimed in claim 6 in which said means for storing and delivering diluent includes a pump, a solenoid valve for pneumatically controlling said pump and said vacuum actuated switch is arranged to energize said valve to operate said pump only when the sealed connection is established and confirmed by operation of said switch means.

10. The combination as claimed in claim 6 in which said means for storing and delivering diluent is a pump, valve means for operating said pump and said microswitch is arranged to energize said valve means for operating said pump only when the carrier reaches a position effecting the sealed connection between the delivery end of the aspirator tube and the collector vessel.

11. The combination as claimed in claim 1 in which said guide means comprise a frame formed of a pair of spaced plate members, said carrier means being accommodated within said frame, means establishing a pivot connection between one end of said carrier means and said frame, matched groove means formed in the frame and pin means on the carrier seatable within said groove means and ridable therewithin, said matched groove means defining the path of movement directing said carrier means first arcuately outwardly of said frame and thence vertically upwardly, the collector vessel being mounted fixedly to the carrier means at the end thereof opposite said one end and positioned to establish said sealed coupling when the carrier means has been reached at a location enabling such coupling.

12. The combination as claimed in claim 11 in which said switch means includes a vacuum check switch coupled to said actuator for enabling of same.

13. The combination as claimed in claim 11 in which said switch means includes a microswitch disposed in the path of said carrier means and engageable therewith only when said carrier means has been moved sufficiently to position the collector vessel in condition sealingly to be coupled to the delivery end of the aspirator tube.

14. The combination as claimed in claim 11 in which said means for storing and delivering diluent includes a pneumatically controlled pump, a solenoid valve controlling the operation of said pump and said check switch is arranged to energize said pump only when the sealed connection is established and confirmed by operation of said check switch.

15. The combination as claimed in claim 11 in which said means for storing and delivering diluent is a pneumatically controlled pump, a solenoid valve controlling the operation of said pump and a microswitch arranged to energize said solenoid-controlled pump only when the carrier reaches a position effecting the sealed connection between the delivery end of the aspirator tube and the collector vessel.

16. The combination as claimed in claim 11 in which said collector vessel comprises a body having a top-opening recess, an internal bore leading from said recess and a resilient insert tightly seated within said recess, said insert having a top-opening cavity and passage means communicating to said bore, the cavity capable of being engaged by the delivery end of the aspirator tube to establish said sealed coupling, and means for ascertaining the establishment of said sealed coupling.

17. The combination as claimed in claim 11 in which said collector vessel comprises a body having a top-opening recess, an internal bore leading from said recess and a resilient insert tightly seated within said recess, said insert having a top-opening recess, an internal bore leading from said recess and a resilient insert tightly seated within said recess, said insert having a top-opening cavity and passage means communicating to said bore, the cavity capable of being engaged by the delivery end of the aspirator tube when said carrier reaches a position to establish said sealed coupling, and means for coupling said source of vacuum to the other end of said internal bore and said switch means includes a vacuum operated check switch coupled to said actuator for enabling of same, and means coupling said vessel to said vacuum source, said means also coupled to said check switch.

18. The combination as claimed in claim 11 in which said collector vessel comprises a body having a top-opening recess, an internal bore leading from said recess and a resilient insert tightly seated within said recess, said insert having a top-opening cavity and passage means communicating to said bore, the cavity capable of being engaged by the delivery end of the aspirator tube when said carrier reaches a position whereat to establish said sealed coupling, means for coupling said source of vacuum to the other end of said internal bore and said switch means includes a microswitch coupled to said control valve actuator and having an actuator disposed in the path of said carrier means and engageable therewith only when said carrier means has reached said position.

19. The combination as claimed in claim 1 and diverter means between the transfer valve and the collector vessel for directing a portion of the rinse liquid emanating from the transfer valve back to the said liquid transfer valve for at least an additional pass therethrough.

* * * * *